Aug. 21, 1962 E. S. BOERNER Plant Pat. 2,167
ROSE PLANT
Filed Oct. 16, 1961
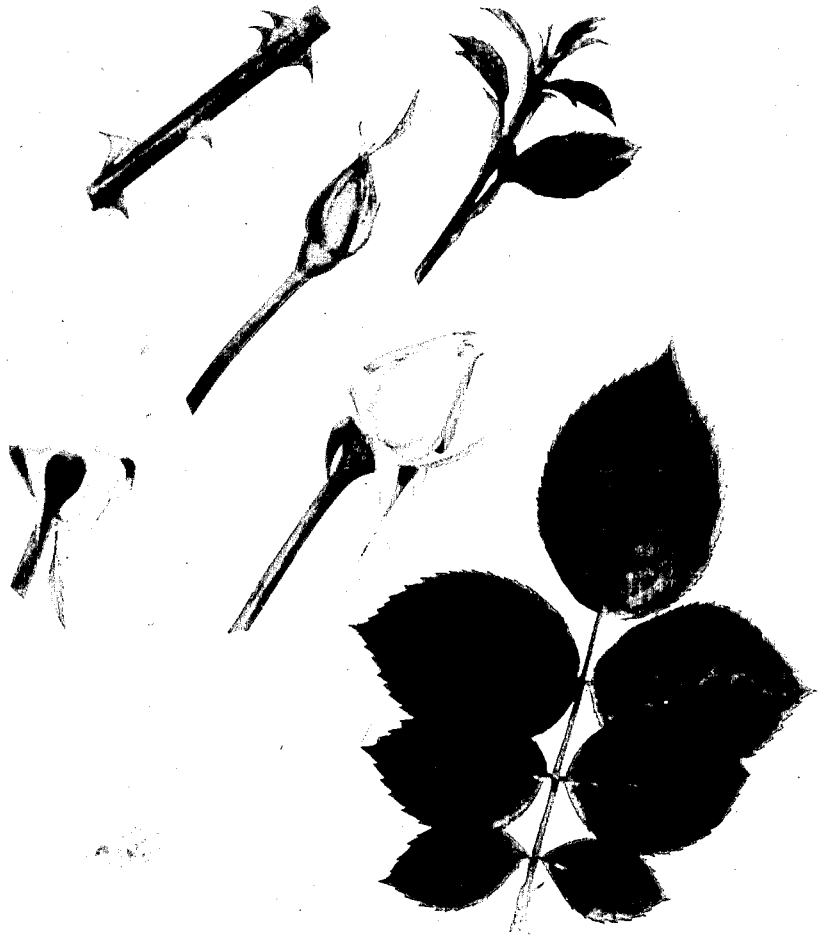
Inventor.
E. S. Boerner
By: Robb & Robb
Attorneys.

United States Patent Office

Plant Pat. 2,167
Patented Aug. 21, 1962

2,167
ROSE PLANT

Eugene S. Boerner, Newark, N.Y., assignor to Jackson & Perkins Company, Newark, N.Y., a corporation of New York Filed Oct. 16, 1961, Ser. No. 145,521
1 Claim. (Cl. 47—61)

The present invention relates to a new and distinct variety of rose plant of the hybrid tea class, which was originated by me by crossing the variety "Golden Masterpiece" (Plant Patent No. 1,284) with the variety "Spartan" (Plant Patent No. 1,357).

The primary objective of this breeding was to produce a new rose variety which has plant and foliage qualities similar to those of the parent variety "Spartan," but which bears flowers of hybrid tea size. This objective was achieved, along with other desirable improvements, as evidenced by the following unique combination of characteristics which are outstanding in the new variety and which distinguish it from its parents, as well as from all other varieties of which I am aware:

(1) A tall habit of plant growth, corresponding to that of the parent variety "Golden Masterpiece";

(2) Full foliage corresponding to that of the parent variety "Spartan";

(3) Large leaf size, with the leaves being even larger than those of the variety "Spartan";

(4) Large flower size, with the shape of the flower generally corresponding to that of the variety "Spartan"; and (5) A distinctive and attractive Pale Yellow-Orange general color tonality of the flowers lightly overcast with Orient Pink in the upper half of the petals, this color being quite different from the flower color of both parent varieties.

Asexual reproduction of my new variety by budding, as performed at Newark, New York, and also at Pleasanton, California, shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: Seedling.
*Seed parent.*—"Golden Masterpiece."
*Pollen parent.*—"Spartan."
Classification:
*Botanic.*—Hybrid tea.
*Commercial.*—Hybrid tea.

*Flower*

(Observations made from specimens grown in a greenhouse at Newark, New York, in the early afternoon during the latter part of the month of March.)

Blooming habit: Recurrent—continuous.
Bud:
*Size.*—Large.
*Form.*—Ovoid; is not affected by wet or hot weather.
*Color.*—When sepals first divide—Scarlet-Red, Plate 1. When petals begin to unfurl—Scarlet, Plate 1, lightly overcast with Rose Doree, Plate 1. When half-blown: inside of petals—Safrano Pink, Plate 2, lightly overcast with Geranium Pink, Plate 1; reverse of petals—Rose Doree, Plate 1, lightly overcast with Orient Pink, Plate 2.
*Sepals.*—Smooth edge; curl back when petals begin to unfurl. Color: inside—Light Turtle Green, Plate 32; outside—Parrot Green, Plate 6.
*Calyx.*—Color—Parrot Green, Plate 6. Shape—apple. Size—large. Aspect—smooth. Odor when rubbed—none.
*Peduncle.*—Length—long. Aspect—rough. Strength—erect; heavy. Color—Oil Green, Plate 5.
*Opening.*—Opens up well; is not affected by adverse weather conditions.
Bloom:
*Size.*—Very large. Average size when full expanded—5¼ inches.
*Borne.*—Several together.
*Stems.*—Long; strong.
*Form (when first open).*—Cupped. Permanence—retains its form to the end, but outer petals curl back.
*Petalage.*—Very double (many petals and stamens hidden). Number of petals under normal conditions—from 55 to 60.
*Color.*—Center of flower—Grenadine Pink, Plate 2, lightly overcast with Orange-Pink, Plate 2. Outer petals—Pale Ochraceous-Salmon, Plate 15, very lightly overcast with Orient Pink, Plate 2, on the outer edge of the petals. Base of petals (aiglet)—Pinard Yellow, Plate 4. Inside of petals—Pale Yellow-Orange, Plate 3, lightly overcast with Orient Pink, Plate 2, in the upper half of the petals. Reverse of petals—Pale Ochraceous-Salmon, Plate 15, lightly overcast with Pale Yellow-Orange, Plate 3. General tonality from a distance—Pale Yellow-Orange, Plate 3, lightly overcast with Orient Pink, Plate 2, in the upper half of the petals.
*Discoloration.*—General tonality at end of first day—Pale Yellow-Orange, Plate 3, lightly overcast with Orient Pink, Plate 2, in the upper half of the petals. Second day—Pale Yellow-Orange, Plate 3, lightly overcast with Orient Pink, Plate 2, in the upper half of the petals. Third day—Pale Ochraceous-Salmon, Plate 15, very lightly overcast with Orient Pink, Plate 2, on the outer edge of the petals.
Petals:
*Texture.*—Thick; is not affected by wet or hot weather.
*Appearance.*—Inside—satiny. Outside—shiny.
*Form.*—Oval.
*Arrangement.*—Imbricated (regularly arranged shingle-like).
*Petaloids in center.*—Few; small.
*Persistence.*—Drop off cleanly.
*Fragrance.*—Moderate. Nature—tea (average hybrid tea scent).
*Lasting quality.*—On the plant—very long. As cut flower—very long.

*Genital Organs*

Stamens, anthers: Medium size; many; regularly arranged around styles. Color—Apricot Yellow, Plate 4.
Stamens, filaments (threads): Medium length. Color—Baryta Yellow, Plate 4.
Pollen: Color—Maize Yellow, Plate 4.
Styles: Bunched; uneven length; medium length; thin; heavy.
Stigmas: Color—Pinard Yellow, Plate 4.
Ovaries: All enclosed in calyx.
Hips: None.
Seeds: None.

*Plant*

Form: Bush.
Growth: Vigorous; upright; tall.
Foliage: Compound of 3–5 leaflets.
*Size.*—Large.
*Quantity.*—Abundant.
*Color.*—New foliage: upper side—Garnet Brown, Plate 1; under side—Van Dyke Red, Plate 13. Old foliage: upper side—Varley's Green, Plate 18; under side—Bice Green, Plate 17.
*Shape.*—Oval.
*Texture.*—Upper side—leathery. Under side—smooth.
*Ribs and veins.*—Ordinary.
*Edge.*—Serrated (saw toothed).
*Serration.*—Double; sharp.
*Leaf stem.*—Color—Jade Green, Plate 31. Under side—prickly.
*Stipules.*—Long; serrated.
Wood:
*New wood.*—Color—Yellowish Oil Green, Plate 5. Bark—smooth.
*Old wood.*—Color—Cress Green, Plate 31. Bark—smooth.

Thorns:
*Thorns.*—Quantity: on main stalks from base—ordinary; on laterals from stalk—ordinary. Form—narrow base; medium length; hooked downward. Color(when young)—Old Rose, Plate 13. Position—irregular.
*Prickles.*—Quantity: on main stalks—none; on laterals—none.
*Short needles.*—Quantity: on main stalks—none; on laterals—none.

I claim:

A new and distinct variety of rose plant of the hybrid tea class, substantially as herein shown and described, characterized particularly as to novelty by the unique combination of a tall habit of plant growth, full foliage of relatively large size, large flower size, with the shape of the flowers generally corresponding to that of the variety "Spartan" (Plant Patent No. 1,357), and a distinctive and attractive Pale Yellow-Orange color tonality of the flowers, lightly overcast with Orient Pink in the upper half of the flower petals.

No references cited.